(12) United States Patent
Denes et al.

(10) Patent No.: US 8,029,902 B2
(45) Date of Patent: Oct. 4, 2011

(54) PLASMA-ENHANCED FUNCTIONALIZATION OF SUBSTRATE SURFACES WITH QUATERNARY AMMONIUM AND QUATERNARY PHOSPHONIUM GROUPS

(75) Inventors: Ferencz S. Denes, Newbury Park, CA (US); Sorin Odisei Manolache, Madison, WI (US); Luis Emilio Cruz-Barba, Guadalajara (MX); Alvaro de Jesus Martinez-Gomez, Guadalajara (MX)

(73) Assignee: Wisconsin Alumni Research Foundation, Madison, WI (US)

( * ) Notice: Subject to any disclaimer, the term of this patent is extended or adjusted under 35 U.S.C. 154(b) by 1108 days.

(21) Appl. No.: 11/609,045

(22) Filed: Dec. 11, 2006

(65) Prior Publication Data

US 2008/0138626 A1    Jun. 12, 2008

(51) Int. Cl.
    *B32B 27/28* (2006.01)
(52) U.S. Cl. ........ 428/412; 428/422; 428/426; 428/446; 428/457; 428/480; 428/522; 428/523; 428/532; 424/409; 427/255.14; 427/255.6; 427/337; 427/569
(58) Field of Classification Search .................. 428/412, 428/422, 426, 446, 457, 480, 522, 523, 532; 424/409, 411; 427/255.14, 255.6, 337, 569
See application file for complete search history.

(56) References Cited

U.S. PATENT DOCUMENTS

| | | | |
|---|---|---|---|
| 2,164,248 A | 6/1939 | Lawrie et al. | |
| 2,559,986 A | 7/1951 | Musser | |
| 4,082,500 A | 4/1978 | Ward et al. | |
| 4,280,824 A | 7/1981 | Lassmann et al. | |
| 4,282,366 A * | 8/1981 | Eudy | 556/413 |
| 4,504,541 A * | 3/1985 | Yasuda et al. | 442/123 |
| 4,568,706 A | 2/1986 | Noetzel et al. | |
| 4,613,517 A | 9/1986 | Williams et al. | |
| 4,720,512 A | 1/1988 | Hu et al. | |
| 4,737,544 A | 4/1988 | McCain et al. | |

(Continued)

FOREIGN PATENT DOCUMENTS

EP    0874242 A1    10/1998

(Continued)

OTHER PUBLICATIONS

Alvarez-Blanco, S., et al., "A Novel Plasma-Enhanced Way for Surface-Functionalization of Polymeric Substrates," Polymer Bulletin 47, pp. 329-336, 2001. Published by Springer-Verlag.

(Continued)

*Primary Examiner* — Callie Shosho
*Assistant Examiner* — John Freeman
(74) *Attorney, Agent, or Firm* — Bell & Manning, LLC

(57) ABSTRACT

Bactericidal substrates and methods of functionalizing the surface of substrates with quaternary ammonium and quaternary phosphonium groups using non-equilibrium RF plasmas are provided. The methods include the step of treating the surface of a substrate with a plasma to create surface active sites. Some methods include the step of reacting the surface active sites with linker molecules, which are then reacted with quaternary ammonium precursor molecules to provide a substrate surface functionalized with quaternary ammonium precursor groups. Other methods react the surface active sites with polymer precursor molecules under plasma conditions to form a covalently-bound polymer layer having reactive sites. The polymer reactive sites are reacted with quaternary phosphonium precursor molecules to provide a substrate surface functionalized with quaternary phosphonium groups. Also provided are bactericidal substrates having immobilized, covalently-bound quaternary ammonium or quaternary phosphonium groups.

11 Claims, 3 Drawing Sheets

U.S. PATENT DOCUMENTS

| | | | |
|---|---|---|---|
| 4,786,556 A | 11/1988 | Hu et al. | |
| 4,803,093 A | 2/1989 | Ishihara et al. | |
| 4,822,681 A | 4/1989 | Schössler et al. | |
| 5,071,909 A | 12/1991 | Pappin et al. | |
| 5,079,156 A | 1/1992 | Mauz et al. | |
| 5,080,924 A | 1/1992 | Kamel et al. | |
| 5,104,649 A | 4/1992 | Jansson et al. | |
| 5,132,108 A | 7/1992 | Narayanan et al. | |
| 5,134,192 A | 7/1992 | Feijen et al. | |
| 5,306,768 A | 4/1994 | Hsu et al. | |
| 5,308,641 A | 5/1994 | Cahalan et al. | |
| 5,316,784 A | 5/1994 | Maurer et al. | |
| 5,336,518 A | 8/1994 | Narayanan et al. | |
| 5,409,696 A | 4/1995 | Narayanan et al. | |
| 5,438,077 A | 8/1995 | Komiya et al. | |
| 5,486,580 A | 1/1996 | Newsham et al. | |
| 5,520,910 A | 5/1996 | Hashimoto et al. | |
| 5,853,744 A | 12/1998 | Mooradian et al. | |
| 5,876,753 A * | 3/1999 | Timmons et al. | 427/488 |
| 5,880,552 A | 3/1999 | McGill et al. | |
| 5,888,591 A | 3/1999 | Gleason et al. | |
| 5,897,955 A | 4/1999 | Drumheller | |
| 6,022,902 A | 2/2000 | Koontz | |
| 6,106,653 A | 8/2000 | Polizzotti et al. | |
| 6,133,436 A | 10/2000 | Koster et al. | |
| 6,143,354 A | 11/2000 | Koulik et al. | |
| 6,159,531 A | 12/2000 | Dang et al. | |
| 6,306,506 B1 | 10/2001 | Timmons et al. | |
| 6,332,363 B1 | 12/2001 | Molloy et al. | |
| 6,402,899 B1 | 6/2002 | Denes et al. | |
| 6,406,921 B1 | 6/2002 | Wagner et al. | |
| 6,440,405 B1 | 8/2002 | Cooper et al. | |
| 6,468,649 B1 | 10/2002 | Zhong | |
| 6,492,445 B2 | 12/2002 | Siddiqui et al. | |
| 6,506,594 B1 | 1/2003 | Barany et al. | |
| 6,528,020 B1 | 3/2003 | Dai et al. | |
| 6,528,264 B1 | 3/2003 | Pal et al. | |
| 6,565,749 B1 * | 5/2003 | Hou et al. | 210/500.38 |
| 6,602,287 B1 | 8/2003 | Millare et al. | |
| 6,602,692 B1 | 8/2003 | Glusenkamp et al. | |
| 6,630,358 B1 | 10/2003 | Wagner et al. | |
| 6,803,069 B2 | 10/2004 | Patnaik et al. | |
| 7,005,031 B2 | 2/2006 | Lucast et al. | |
| 7,112,615 B2 | 9/2006 | Gleason et al. | |
| 7,276,283 B2 | 10/2007 | Denes et al. | |
| 2002/0110932 A1 | 8/2002 | Wagner et al. | |
| 2002/0128234 A1 | 9/2002 | Hubbell et al. | |
| 2003/0113478 A1 | 6/2003 | Dang et al. | |
| 2003/0163198 A1 | 8/2003 | Morra et al. | |
| 2003/0207099 A1 | 11/2003 | Gillmor et al. | |
| 2004/0251188 A1 * | 12/2004 | Skinner et al. | 210/198.2 |
| 2008/0093310 A1 * | 4/2008 | Yeh et al. | 210/767 |
| 2009/0123639 A1 | 5/2009 | Denes et al. | |

FOREIGN PATENT DOCUMENTS

| | | |
|---|---|---|
| WO | WO 01/83826 | 11/2001 |
| WO | WO 01/96452 | 12/2001 |
| WO | WO 03/083477 | 10/2003 |

OTHER PUBLICATIONS

Marchisio, M.A., et al., "A comparison between the hemolytic and antibacterial activities of new quaternary ammonium polymers," J. Biomater. Sci. Polymer Edn., vol. 6, No. 6, pp. 533-539 (Jan. 17, 1994).

Tiller, Joerg, "Designing surfaces that kill bacteria on contact," PNAS, vol. 98, No. 11, pp. 5981-5985 (May 22, 2001).

Tashiro, T, "Antibacterial and Bacterium Absorbing Macromolecules," Macromol. Mater. Eng., vol. 286, No. 2 (2001).

Lin, J., et al., "Insights into bactericidal action of surface-attached-poly(vinyl-N-hexylpyridium) chains," Biotechnology Letters, vol. 24, pp. 801-805, 2002.

Kenawy, E.R., et al., "Biologically Active Polymers. V. Synthesis and Antimocrobial Activity of Modified Poly(glycidyl methacrylate-co-2-hydroxyethyl methacrylate) Derivatives with Quaternary Ammonium and Phosphonium Salts," Journal of Polymer Science: Part A: Polymer Chemistry, vol. 40, 2384-2393 (2002).

Popa, A., et al., "Study of quaternary 'onium' salts grafted on polymers: antibacterial activity of quaternary phosphonium salts granted on 'gel-type' styrene-divinylbenzene copolymers," Reactive and Functional Polymers, vol. 55, Issue 2, pp. 151-158 (Apr. 2003).

Kenawy, E.R., et al., "Biologically Active Polymers, 6$^a$: Synthesis and Antimicrobial Activity of Some Linear Copolymers with Quaternary Ammonium and Phosphonium Groups," Macromol. Biosci., vol. 3, No. 2, (2003).

Final Office Action for U.S. Appl. No. 10/809,318, mailed Jul. 13, 2009.

McKelvey, et al., "Reaction of Epoxides with Cotton Cellulose in the Presence of Sodium Hydroxide," Textile Research Journal (1959), 29, 918-925.

Francis, Thomas et al, "The Base-Catalyzed Condensation of Cellulosic Fabrics with Volatile Epoxides," Textile research Journal (1963), 33:8, 583-599.

Ferrante, Gerald R., "A Vapor-Phase Epichlorhydrin Process for Wet and Dry Wrinkle Recovery" Textile Research Journal (1965), 35:5, 446-452.

McKelvey, John B. et al, "The Action of Epichlorohydrin in the Presence of Alkalies and Various Salts on the Crease Recovery of Cotton." Journal of Applied Polymer Science (1963) 7: 1371-1389.

McKelvey, John B. et al., "Reaction of Cotton Cellulose with Epoxides in the Presence of Acid Catalysts," American Dyestuff Reporter (1960), 49:22, 19-24.

Panchalingam et al., Molecular surface tailoring of biomaterials via pulsed RF plasma discharges, Part I.A.: Surface Modification, Characterization, and Properties: RF Plasma Gas Discharge, accepted Dec. 15, 1992, pp. 3-17.

Notice of Allowance for U.S. Appl. No. 10/809,318 mailed Jan. 11, 2010.

U.S. Appl. No. 11/609,045, filed Mar. 24, 2004, Denes et al.

Non-final Office Action for U.S. Appl. No. 10/807,914, mailed Oct. 11, 2005.

Non-final Office Action for U.S. Appl. No. 10/807,914, mailed Jun. 1, 2006.

Non-final Office Action for U.S. Appl. No. 10/807,914, mailed Nov. 30, 2006.

Notice of Allowance for U.S. Appl. No. 10/807,914, mailed May 30, 2007.

Non-final Office Action for U.S. Appl. No. 10/809,318, mailed Jul. 25, 2006.

Final Office Action for U.S. Appl. No. 10/809,318, mailed Apr. 10, 2007.

Non-final Office Action for U.S. Appl. No. 10/809,318, mailed Nov. 2, 2007.

Final Office Action for U.S. Appl. No. 10/809,318, mailed Jul. 23, 2008.

Non-final Office Action for U.S. Appl. No. 10/809,318, mailed Feb. 3, 2009.

Rasmussen, et al., "Covalent Immobilization of DNA into Polystyrene Microwells: The Molecules are only Bound at the 5' End," Analytical Biochemistry, 198, pp. 138-142, 1991. Published by Academic Press, Inc.

Timofeev, et al., "Regioselective Immobilization of Short Oligonucleotides to Acryl Copolymer Gels," Nucleic Acids Research, 24, No. 16, pp. 3142-3148, 1996. Published by Oxford University Press.

Proudnikov, et al., "Chemical Methods of DNA and RNA Fluorescent Labeling," Nucleic Acids Research, 24, No. 22, pp. 4535-4532, 1996. Published by Oxford University Press.

Parinov, et al., DNA Sequencing by Hybridization to Microchip Octa- and Decanucleotides Extended by Stacked Pentanucleotides, Nucleic Acids Research, 24, No. 15, pp. 2998-3003, 1996. Published by Oxford University Press.

Guschin et al., Manual Manufacturing of Oligonucleotide, DNA, and Protein Microchips, Analytical Biochemistry, 250, pp. 203-211, 1997. Published by Academic Press.

Fotin et al., "Parallel Thermodynamic Analysis of Duplexes on Oligodeoxyribonucleotide Microchips," Nucleic Acids Research, 26, No. 6, pp. 1515-1521, 1998. Published by Oxford University Press.

Proudnikov et al., Immobilization of DNA in Polyacrylamide Gel for the Manufacture of DNA and DNA-Oligonucleotide Microchips, *Analytical Biochemistry*, 259, pp. 34-41, 1998. Published by Academic Press.

Wang, et al., "Polishable and Renewable DNA Hybridization Biosensors," *Anal Chem*, 70, pp. 3699-3702, 1998. Published by the American Chemical Society.

Ivanova, et al., "Feasibility of Using Carboxylic-rich Polymeric Surfaces for the Covalent Binding of Oligonucleotides for microPCR Applications." Smart Mater. Struct., 11, pp. 783, 2002. Published by Institute of Physics Publishing.

Metzger et al., Signal to Noise Comparison Accelr8 OptArray vs. The Leading Polymer and Silane Microarray Slide Chemistries, *Technical Bulletin*, No. TB0400, 2002.

Yang et al., "DNA-modified Nanocrystalline Diamond Thin-films as Stable, Biologically Active Substrates," *Nature Materials*, 1, No. 4, pp. 253-257, 2002. Published by Nature Publishing Group.

Liu et al., "DNA Probe Attachment on Plastic Surfaces and Microfluidic Hybridization Array Channel Devices with Sample Oscillation," *Analytical Biochemistry* 317, pp. 76-84, 2003. Published by Academic Press.

http://www/vwrcanlab.com Website, "A Specific Surface for a Specific Application," (see pp. 42-47).

Podyminogin et al., "Attachment of Benzaldehyde-modified Oligodeoxynucleotide Probes to Semicarbazide-Coated Glass," *Nucleic Acids Research*, vol. 29, No. 24, pp. 5090-5098, 2001. Published by Oxford University Press.

Cheung et al., "5'-Thiolated Oligonucleotides on (3-Mercaptopropyl) trimethoxysilaten-Mica: Surface Topography and Coverage," printed from Web, Jun. 5, 2003. Published by American Chemical Society.

"Motorola Goes for Organic Growth with Biochips," http://www.groupweb.com/sci_tech/jun_30/motorola.html. Website article printed on Jan. 2, 2000.

M. Quan, "Motorola's Biochip Center Aims for a Healthier World," *EE Times*, Feb. 16, 1999. http://www.edtn.com/story/tech/OEG19990216S0030-R. Website article printed on Aug. 6, 2004.

"EasySpot Microarray Slide," http://www.u-vision-biotech.com/english/product_service/easy_oligo. Website article printed on Feb. 19, 2004.

"Novel surface chemistry for DNA immobilization," http://hamers.chem.wisc.edu/research/bioattachment/dna_on_silicon.htm. Website article printed on Mar. 2, 2003.

"Motorola and Packard to produce 'biochips'" http://www4.nando.net/newsroom/ntn/health/062998/health7_12937_noframes.html. Website article printed on Jan. 2, 2000.

"Biochip," http://www.whatis.com/biochip.html. Website article printed on Jan. 2, 2000.

"New "Biochips" Aimed at Medicine, Agriculture," http://www.pcworld.com/pcwtoday/article/0,1510,7313,00.html. Website article printed on Jan. 2, 2000.

"Microarray Substrates & Slides," http://arrayit.com/Products/Substrates/. Website article printed on Aug. 9, 2004.

"Super Epoxy Substrates," http://arravit.com/Products/Substrates/SME/sme.html. Website article printed on Aug. 6, 2004.

Material Safety Data Sheet for Epichlorohydrin, MSDS Number: E0925, Jan. 1, 1996, Mallinckrodt Baker, Inc., Phillipsburgh, NJ, pp. 1-9.

"Biomolecule Immobilization," http://www.surmodics.com/pageDetail.aspx?pageId=10&menuID=10, Website article printed on Feb. 19, 2004.

"Photolink Manufacturing Process," http://www.surmodics.com/pageDetail.aspx?pageId=7&menuID=7, Website article printed on Feb. 19, 2004.

"A Specific Surface for a Specific Application," http://www/vwrcanlab.com, Website article printed prior to Mar. 24, 2004.

Denes et al., "Mechanism of RF Plasma Induced Fragmentation of $SiCl_4$ and Surface Functionalization of Polymeric Substrates from $SiCl_x$ Species," Journal of Applied Polymer Science, 1996, vol. 61, pp. 875-884.

International Search Report dated Aug. 31, 2006 for PCT/US2005/006514.

W. C. J. Ross, "The Reactions of Certain Epoxides in Aqueous Solutions," *J. Chem. Soc.*, pp. 2257-2272 (1950).

G. N. Merrill, "The gas-phase reactivity of epichlorohydrin with hydroxide," *Journal of Physical Organic Chemistry* 17:241-248 (2004).

* cited by examiner

PLASMA-ENHANCED FUNCTIONALIZATION OF SUBSTRATE SURFACES WITH QUATERNARY AMMONIUM AND QUATERNARY PHOSPHONIUM GROUPS

STATEMENT OF GOVERNMENT RIGHTS

This invention was made with United States government support awarded by the following agency: USDA/CSREES under grant number 2004-35201-14121. The United States government has certain rights in this invention.

FIELD OF THE INVENTION

This invention pertains generally to the functionalization of substrate surfaces with quaternary ammonium and quaternary phosphonium groups using non-equilibrium radio frequency (RF) plasmas.

BACKGROUND OF THE INVENTION

Concern about microbial contamination of surfaces is widespread, especially in the medical and food industries. Conventional antibacterial agents, including solids, liquids, and gaseous disinfectants based on low molecular weight compounds, suffer from residual toxicity that can lead to equally serious medical and environmental problems. Polymeric antimicrobial materials are non-volatile, more chemically stable, and less likely to permeate skin than their low molecular weight counterparts. Incorporation of antibacterial macromolecules into hydrogels or rubbers, however, does not eliminate residual toxicity behavior. Therefore, covalent attachment of compounds with antibacterial functionalities, such as quaternary ammonium and quaternary phosphonium groups, onto inert polymer surfaces is desirable.

The bactericidal activity of low and high molecular weight antimicrobial agents having quaternary ammonium and quaternary phosphonium groups has been demonstrated. (See S. Tan, G. Li, J. Shen, Y. Liu, M. Zong, J. Appl. Polym. Sci., 77, 1869, (2000); E. R. Kenawy, and G. Wnek, Prog. Polym. Sci., submitted 2002; Y. Chen, X, Wang, B. Li, Series of water-insoluble polymeric quaternary phosphonium salt used for bactericides, U.S. Pat. No. 6,261,538 B1, issued Jul. 17, 2001; C. J. Bradaric-Baus, Y. Zhou, Phosphonium salts and methods for their preparation, International Publication Number: WO 2004/094438 A1, E. R. Kenawy, J. Appl. Polym. Sci., 82, 1364, (2001); E. R. Kenawy and F. I. Abdel, A. R, El-Shansboury, and M. H. El-Newehy, J. Controlled Release, 50,145, (1998); W. K. Whitekettle, G. J. Tafel, Control of protozoa and protozoan cysts that harbor legionella, U.S. Pat. No. 6,579,859, issued Jun. 17, 2003; M. A. Marchisio, P. Bianciardi, T. Longo, P. Ferruti, E. Ranucci, and M. G. Neri, A comparison between the hemolytic and antibacterial activities of new quaternary ammonium polymers, J. Biomater. Sci. Polymer Edn, 6, 533-539 (1994).)

Others have studied the antibacterial activity of polymers having quaternary ammonium and quaternary phosphonium groups. In one study, novel quaternary ammonium polymers were prepared by alkylation of tertiary amino precursors. The antibacterial and hemolytic activities of the polymers were compared with the properties of low molecular weight quaternary ammonium salts. Some of the polymers demonstrated antibacterial activity comparable to the low molecular weight quaternary ammonium compounds but exhibited significantly less or virtually absent hemolytic behavior. (See M. A. Marchisio, P. Bianciardi, T. Longo, P. Ferruti, E. Ranucci, and M. G. Neri, A comparison between the hemolytic and antibacterial activities of new quaternary ammonium polymers, J. Biomater. Sci. Polymer Edn, 6, 533-539 (1994).)

In another study, copolymers synthesized from 2-chloroethyl vinyl ether (CEVE) and methyl methacrylate (MMA), 2-hydroxyethyl methacrylate (HEMA), or vinylbenzyl chloride (VBC) were quaternarized using triethylamine, triphenylphosphine or tributylphosphine and the antibacterial activity of the resulting polycationic biocides was evaluated. (See E. R. Kenawy and Y. A. G. Mahmoud, Synthesis and antimicrobial activity of some linear copolymers with quaternary ammonium and phosphonium groups, Macromol. Biosci. 3, 107-16, (2003).) The phosphonium-containing biocides were more effective against bacteria than the ammonium-containing copolymers. In addition, the antibacterial activity was found to increase as the number of phosphonium units in the copolymer increased. The increase in charge density may facilitate the incorporation of the biocide into bacteria cells, leading to potassium ion leakage and, eventually, cell death.

In another study, the copolymer poly(glycidyl methacrylate-co-2-hydroxyethyl methacrylate) was functionalized with chloromethyl groups using chloroacetyl chloride and subsequently converted to a quaternary ammonium or quaternary phosphonium salt. (See E. R. Kenawy, F. I. Abdel-Hay, A B D El-Raheem, R. El-Shanshoury, and M. H. El-Newehy, Biologically active polymers. V. Synthesis and antimicrobial activity of modified poly(glycidyl methacrylate-co-2-hydroxyethyl methacrylate) derivatives with quaternary ammonium and phosphonium salts, J. Polym. Sci, Part A: Polymer Chemistry, 40, 2384-2393, (2002).) The antibacterial activity of the resulting polycations was evaluated against gram-negative bacteria (*Escherichia coli*, *Pseudonomas aeruginosa*, *Shigella* sp., and *Salmonella typhae*), gram-positive bacteria (*Bacillus subtilus* and *B. cereus*) and fungus (*Trichophyton rubrum*). All of the copolymers exhibited high antibacterial activity but the quaternary phosphonium salt synthesized from tributylphosphine was the most effective against both gram negative and positive bacteria and the fungus *T. rubrum*.

Others have used wet-chemistry techniques to functionalize surfaces with quaternary ammonium and quaternary phosphonium containing compounds. In one study, poly(4-vinyl-N-alkylpyridinum bromide) was covalently attached to glass slides and the antibacterial properties evaluated. (See J. C. Tiller, C. J. Liao, K. Lewis, and A. M. Klibanov, Designing surfaces that kill bacteria on contact, PNAS, 98, 5981-5985, (2001).) Amino glass slides were functionalized by either acylation with acryloyl chloride, graft copolymerization with 4-vinylpyridine, and N-hexylation with hexyl bromide, or by the attachment of partially N-hexylated poly(4-vinylpyridine). The modified surfaces killed more than 90% of *S. aureus* cells deposited onto the surface of the slides and more than 99% of deposited *S. epidermidis*, *P. aeruginosa*, and *E. coli* cells in a dry state. The antibacterial activity of the surface-bound polycations was thought to be due to the disruption of the outer cell membranes of bacteria and/or penetration of the inner cell membranes followed by leakage of cellular contents.

In another study, wet-chemical techniques were used to graft quaternary phosphonium salts onto macromolecular supports. (See A. Popa, C. M. Davidescu, R. Trif, Gh. Ilia, S. Iliescu, and Gh. Dehelean, Study of quaternary 'onium' salts grafted on polymers: antibacterial activity of quaternary phosphonium salts grafted on 'gel-type' styrene-divinylbenzene copolymers, Reactive and Functional Polymers, 55, 151-158, (2003).) Various alkyl phosphine derivatives were used to quaternize the support copolymer including triethyl, tributyl, tripropyl, triphenyl, methyldiphenyl, dimethylphenyl, ethyldiphenyl, and diethylphenyl phosphine compounds. All of the modified supports exhibited antibacterial activity against *S. aureus, E. coli* and *P. aeruginosa*, although the bactericidal efficiencies depended upon the nature of the alkyl groups connected to the phosphonium ions. Surfaces functionalized with the ethylphosphonium compounds showed the strongest antibacterial activity.

Another study demonstrated that polyethylene slides nano-coated with silica and subsequently derivatized with long-chain poly(vinyl-N-hexylpyridinium) become permanently bactericidal. (See J. Lin, J. C. Tiller, S. B. Lee., K. Lewis, A. M. Klibanov, Insights into bactericidal action of surface-attached poly(vinyl-N-hexylpyridinium) chains, Biotechnology Letters, 24, 801-805, (2002).) The modified polyethylene surfaces were able to kill 90-99% of both airborne and waterborne wild-type and antibiotic-resistant strains of the human pathogen *Staphylococcus aureus*.

Finally, a recent review of antibacterial and bacterium adsorbing macromolecules emphasized the importance of polymeric biocides for the development of novel surfaces that kill bacteria on contact. (See T. Tashiro, Antibacterial and bacterium adsorbing macromolecules, Macromol. Mater. Eng, 286, 63-87, (2001).) The article describes the immobilization and antibacterial activity of iodine, quaternary ammonium salts, antibiotics, and other antibacterial groups to macromolecular substrates. The synthesis of polycationic polymers with quaternary ammonium salts, biguanide groups, quaternary pyridium salts, sulphonium salts, phosphonium salts, and other antibacterial groups are also discussed. The use of bacterium adsorbing macromolecules based on poly(4-vinylpyridine-co-divinylbenzene), crosslinked poly(3- and 4-chloromethylated styrene-g-amine), and poly(glycidyl methacrylate-g-amine) as well as filters and microporous membranes coated with quaternized poly(4-vinylpyridine-co-styrene) as disinfectants are also evaluated.

Although the prior art describes the use of wet-chemistry techniques to synthesize bactericidal polymers and to immobilize the polymers on the surface of substrates, the use of non-equilibrium, radio frequency (RF) plasmas to functionalize a wide variety of substrates with quaternary ammonium and quaternary phosphonium groups has not yet been accomplished.

SUMMARY OF THE INVENTION

This invention provides bactericidal substrates and methods of functionalizing the surface of a substrate with quaternary ammonium and quaternary phosphonium groups using non-equilibrium RF plasmas. The plasma-chemist approach to surface functionalization offers a number of advantages over wet-chemistry techniques. First, the charged and neutral species of low- and atmospheric-pressure plasmas have energy levels comparable to common bond energies. Consequently, even the most inert polymer surfaces can be efficiently covalently functionalized. Second, plasma-functionalization reactions are heterogeneous dry processes and as a result, require only minimal precursor material for surface functionalization. The small amount of materials used, the elimination of the need for vacuum pumps, the fast functionalization reactions, and the minimal energy requirements make plasma processes very cost effective. Finally, the plasma chemistry approach is an environmentally benign process and any potentially toxic, volatile reaction by-products can be easily trapped and neutralized.

The methods provided herein are well suited for the production of bactericidal substrates potentially useful in a variety of applications, such as food processing, medical, and biotechnology applications. In addition, the methods and substrates are expected to be useful to provide bactericidal materials for space-travel applications.

The plasma treatments of the present invention are used to create active sites directly on substrate surfaces and in some embodiments, to form a covalently-bound polymer layer having reactive sites on substrate surfaces. In one variation of the method, substrate surface active sites are reacted with linker molecules in situ in the absence of plasma to provide surface-bound linker molecules. The linker molecules are then reacted with quaternary ammonium precursor molecules to form quaternary ammonium functionalized molecules covalently bound to the surface of the substrate.

In another embodiment of the method, substrate surface active sites are reacted with polymer precursor molecules by exposing the substrate surface to a plasma of polymer precursor molecules. The reaction forms a layer of a polymer comprising reactive sites covalently bound to the substrate surface. The polymer reactive sites are then reacted with quaternary phosphonium precursor molecules to generate a quaternary phosphonium functionalized polymer layer covalently bound to the surface of the substrate.

In yet another embodiment of the method, substrate surface active sites are reacted with linker precursor molecules by exposing the substrate surface to a plasma of linker precursor molecules to provide linker molecules covalently bound to the substrate surface. These surface-bound linker molecules are then reacted with polymer precursor molecules to form a layer of polymer comprising amine groups. The amine functionalities are converted to quaternary ammonium groups via alkylation of the amine groups on the surface-bound polymers. If the substrate is capable of reacting with the polymer precursor molecules, the step of reacting with the linker precursor molecules may be omitted.

The invention also provides bactericidal substrates functionalized with quaternary ammonium or quaternary phosphonium groups. In one embodiment, the bactericidal substrate comprises quaternary ammonium functionalized molecules covalently bound to the surface of the substrate, the quaternary ammonium functionalized molecules desirably comprise hydroxyl functionalized alkyl chains terminated with quaternary ammonium groups. In another embodiment, the bactericidal substrate comprises a quaternary phosphonium functionalized polymer layer covalently bound to the surface of the substrate, wherein the quaternary phosphonium functionalized polymer is desirably the reaction product of allyl halide monomers and quaternary phosphonium precursor molecules having the formula $PR_1R_2R_3$, wherein $R_1$, $R_2$ and $R_3$ are independently selected from the group consisting of linear or branched alkyl groups, aryl groups, aralkyl groups, and alkyl, aryl or aralkyl groups substituted with a hydroxyl group or an alkoxy group. In yet another embodiment, the bactericidal substrate comprises a quaternary ammonium functionalized polymer layer covalently bound to the surface of the substrate, wherein the polymer layer is covalently anchored to the surface of the substrate via —Si—O— bonds.

In general, substrates suitable for the methods and compositions provided herein include a wide range of polymers, metals, and glasses. Specific examples of substrates include polyethylene, polypropylene, polyacetal, polyester terephthalate, polytetrafluoroethylene, polycarbonate, polystyrene, polymethylmethacrylate, silicone rubber, cellulose, paper, glass and stainless steel substrates.

Further objects, features, and advantages of the invention will be apparent from the following detailed description when taken in conjunction with the accompanying drawings.

DETAILED DESCRIPTION OF THE INVENTION

This invention provides bactericidal substrates and methods of functionalizing the surface of a substrate using non-equilibrium RF plasmas. The plasma treatments are used to create active sites directly on substrate surfaces and in some embodiments, to form a covalently-bound polymer layer having reactive sites on substrate surfaces. As used herein, the term "active site" refers to a site on the surface where a free-radical or charge has been created by exposure to a plasma.

In certain embodiments, substrate surface active sites are reacted with linker molecules in situ in the absence of plasma. The linker molecules are then reacted with precursor molecules to form quaternary ammonium functionalized molecules covalently bound to the surface of the substrate. In other embodiments, substrate surface active sites are reacted with polymer precursor molecules by exposing the substrate surface to a plasma formed from polymer precursor molecules to form a layer of a polymer covalently bound to the substrate surface. The resulting polymer has reactive sites which are then reacted with quaternary phosphonium precursor molecules to generate a quaternary phosphonium functionalized polymer layer covalently bound to the substrate surface As used herein, the term "reactive site" refers to any functional group that is capable of reacting with a quaternary phosphonium precursor molecule to form a quaternary phosphonium-functionalized polymer. The resulting quaternary ammonium and quaternary phosphonium containing bactericidal substrates are also encompassed by the present invention. In still other embodiments, substrate surface active sites are reacted with linker precursor molecules in a plasma whereby linker molecules are covalently bound to the surface. These linker molecules are then reacted with polymer precursor molecules to form a polymer having amine groups covalently bound to the surface via the linker molecules. The amine groups on the polymer are then alkylated to provide a quaternary ammonium functionalized polymer.

The methods of the present invention make use of non-equilibrium RF plasmas. Plasma treatment of substrate surfaces may be conducted in any suitable plasma reactor. Many such reactors are well-known and commercially available. Suitable reactors include continuous plasma reactors, low-pressure plasma reactors, and atmospheric-pressure plasma reactors. One such reactor is described in detail in U.S. patent application Ser. No. 10/807,914, filed Mar. 24, 2004, the entire disclosure of which is incorporated herein by reference. The selection of appropriate plasma parameters for the creation of active sites on substrate surfaces or for polymer deposition on substrate surfaces may depend on a variety of factors, including reactor type and the nature of the substrate surface to be treated. Some typical reactor conditions are described in the Examples below.

Figure 1:
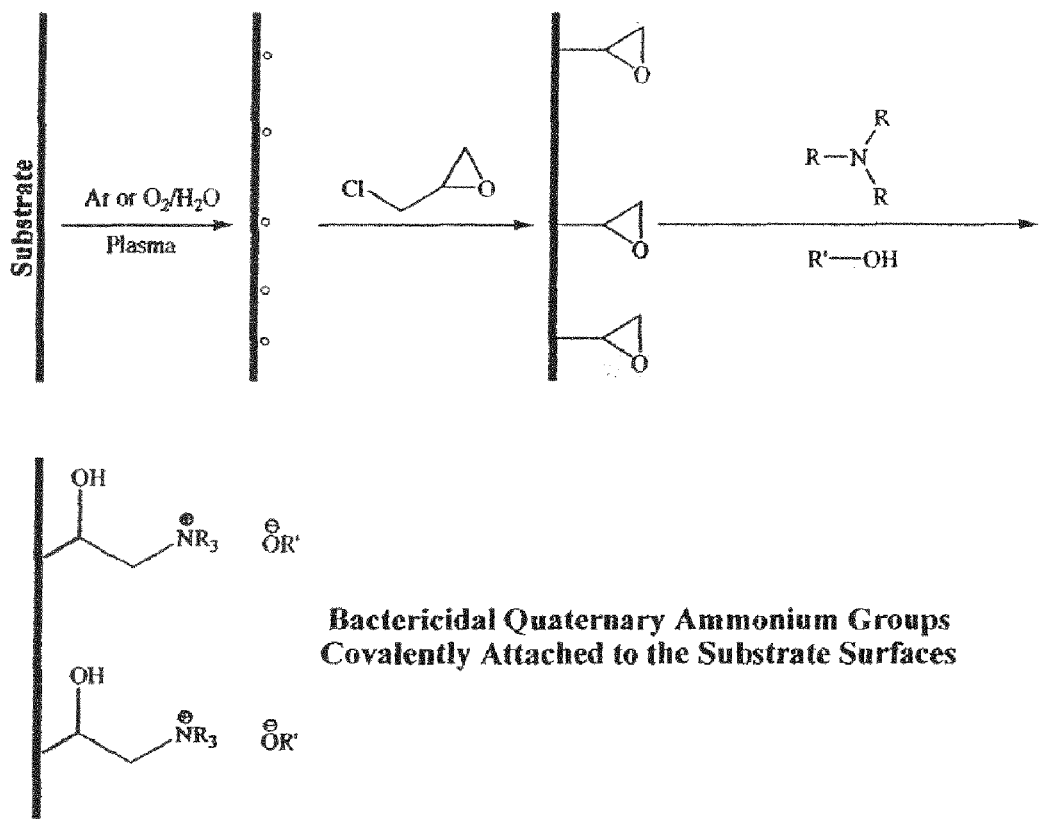
FIG. 1 shows a reaction pathway for the functionalization of the surface of a substrate with quaternary ammonium groups.

In one embodiment of the present invention, the method for functionalizing the surface of a substrate comprises the three steps illustrated in FIG. 1. In a first step, the substrate surface is exposed to a plasma under conditions that promote the formation of active sites, such as free-radicals and/or ions, on the surface of the substrate. The plasma in the first step is desirably an inert plasma which, for the purposes of this disclosure, is a plasma that creates active sites on the substrate surface without introducing chemical functional groups, such as hydroxyl groups, onto the surface.

In a subsequent step, the active sites are reacted with a gas containing linker molecules in the absence of plasma. The linker molecules are capable of forming covalent bonds to the plasma-treated substrate surface. In some embodiments, the linker molecules will be epoxy-functional molecules. Epoxy-functional molecules are molecules that contain an oxirane or epoxy group, such as an epihalohydrin. Suitable linker molecules include epichlorohydrin, epibromohydrin, epifluorophydrin, or combinations thereof. This step of the method may be accomplished by exposing the plasma-treated surface to the gas containing linker molecules in situ, that is, without first breaking the vacuum in the plasma reactor chamber or otherwise exposing the surface to the atmosphere.

In a following step of the method, the surface-bound linker molecules are reacted with quaternary ammonium precursor molecules. The quaternary ammonium precursor molecules are capable of forming covalent bonds to the surface-bound linker molecules to form quaternary ammonium functionalized molecules. The binding of the precursor molecules to the surface-bound linker molecules provides a substrate surface functionalized with quaternary ammonium groups. These quaternary ammonium functionalized molecules are relatively short-chain organic molecules that are covalently bonded to the substrate surface at one end and terminated by a quaternary group at the opposite end and, as such, are distinguishable from quaternary ammonium polymers having multiple quaternary ammonium groups along their polymer backbone. In some embodiments, the quaternary ammonium precursor molecules have the formula $NR_1R_2R_3$, wherein $R_1$, $R_2$ and $R_3$ are independently selected from the group consisting of linear or branched alkyl groups, aryl groups, aralkyl groups, and alkyl, aryl or aralkyl groups substituted with a hydroxyl group or an alkoxy group. Suitable quaternary ammonium precursor molecules also include triethylamines, triphenylamines, or combinations thereof The present invention also provides bactericidal substrates functionalized with quaternary ammonium groups. In one embodiment, the bactericidal substrate comprises quaternary ammonium functionalized molecules covalently bound to the substrate surface, the quaternary ammonium functionalized molecules comprising hydroxyl functionalized alkyl chains terminated with quaternary ammonium groups. The covalently-bound quaternary ammonium functionalized molecules may have the formula $-(CH_2)_n-CH(OH)-(CH_2)_m-NR_1R_2R_3$, wherein n is an integer from 0 to 20 (e.g., 0 to 10), m is an integer from 1 to 20 (e.g., 0 to 10), and $R_1$, $R_2$ and $R_3$ are independently selected from the group consisting of linear or branched alkyl groups, aryl groups, aralkyl groups, and alkyl, aryl or aralkyl groups substituted with a hydroxyl group or an alkoxy group.

Figure 2:
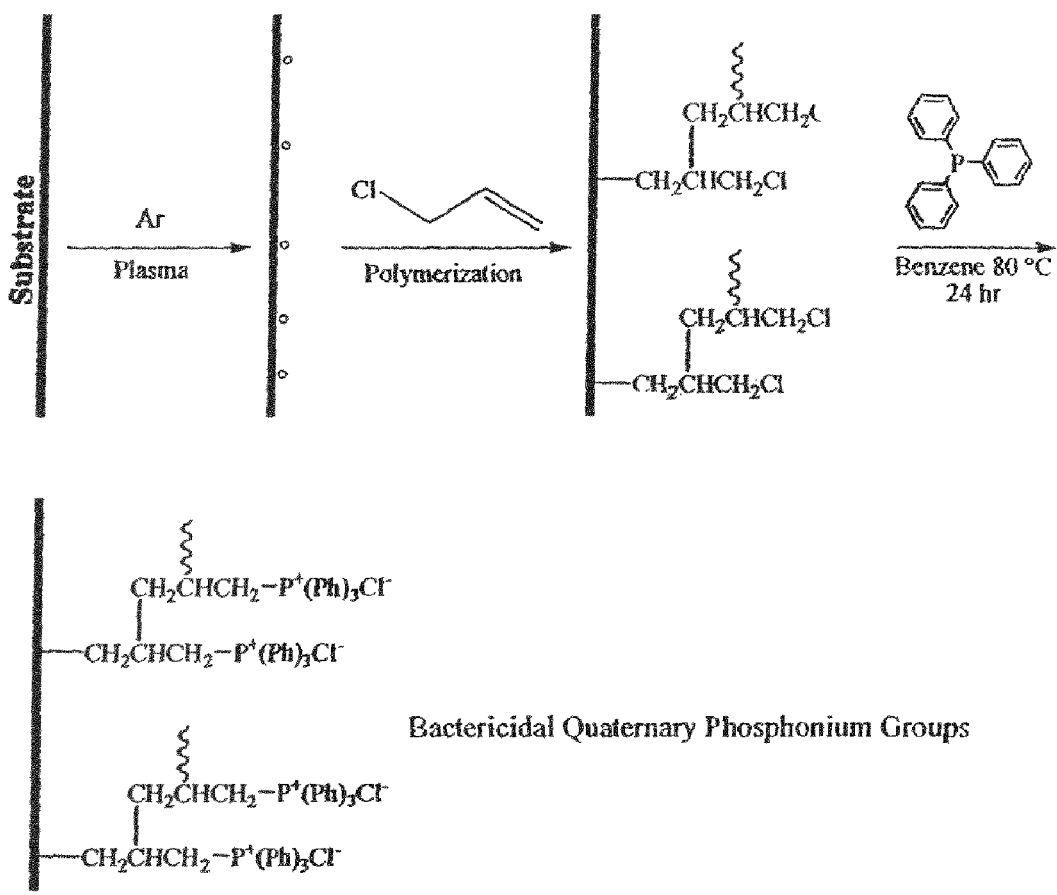
FIG. 2 shows a reaction pathway for the functionalization of the surface of a substrate with quaternary phosphonium groups.

In another embodiment of the present invention, the method for functionalizing the surface of a substrate comprises the steps shown in FIG. 2. First, the substrate surface is exposed to an inert plasma under conditions that promote the formation of active sites, such as free-radicals and/or ions, on the surface of the substrate. Suitable inert plasmas include plasmas formed from inert gases, such as argon (Ar).

In a subsequent step, the substrate surface active sites are reacted with polymer precursor molecules by exposing the activated substrate surface to a plasma of polymer precursor molecules under conditions which promote the covalent attachment of a polymer layer comprising reactive sites to the surface of the substrate. The polymer precursor molecules are capable both of forming covalent bonds to the plasma-treated substrate and of polymerizing to create a polymer layer comprising reactive sites. In some embodiments, the polymer precursor molecules comprise allyl halide monomers. An example of a suitable allyl halide is allyl chloride. In such an embodiment, the reactive sites are chlorine groups.

In a following step of the method, the polymer reactive sites are reacted with quaternary phosphonium precursor molecules in the absence of plasma. This step may take place ex situ, that is, by venting the reactor chamber to bring it up to atmospheric pressure and exposing the reactive sites to selected precursor molecules under conditions which promote covalent bond formation. Suitable methods for functionalizing the polymer with quaternary phospohium groups are describe in Example 3, below. The binding of the precursor molecules to the reactive sites on the polymer layer provides a quaternary phosphonium functionalized polymer layer covalently bound to the substrate surface. Through this covalently attached polymer layer, the surface of the substrate becomes functionalized with quaternary phosphonium groups. In some embodiments, the quaternary phosphonium precursor molecules have the formula $PR_1R_2R_3$, wherein $R_1$, $R_2$ and $R_3$ are independently selected from the group consisting of linear or branched alkyl groups, aryl groups, aralkyl groups, and alkyl, aryl or aralkyl groups substituted with a hydroxyl group or an alkoxy group. Suitable quaternary phosphonium precursor molecules include triphenylphosphine, tributylphosphine, or combinations thereof.

The present invention also provides bactericidal substrates functionalized with quaternary phosphonium groups. In one embodiment, the bactericidal substrate comprises a quaternary phosphonium functionalized polymer layer covalently bound to the surface of the substrate, wherein the quaternary phosphonium functionalized polymer is the reaction product of allyl halide monomers and quaternary phosphonium precursor molecules having the formula $PR_1R_2R_3$, wherein $R_1$, $R_2$ and $R_3$ are independently selected from the group consisting of linear or branched alkyl groups, aryl groups, aralkyl groups, and alkyl, aryl or aralkyl groups substituted with a hydroxyl group or an alkoxy group. In some embodiments, the allyl halide monomers comprise allyl chloride monomers.

Figure 3:
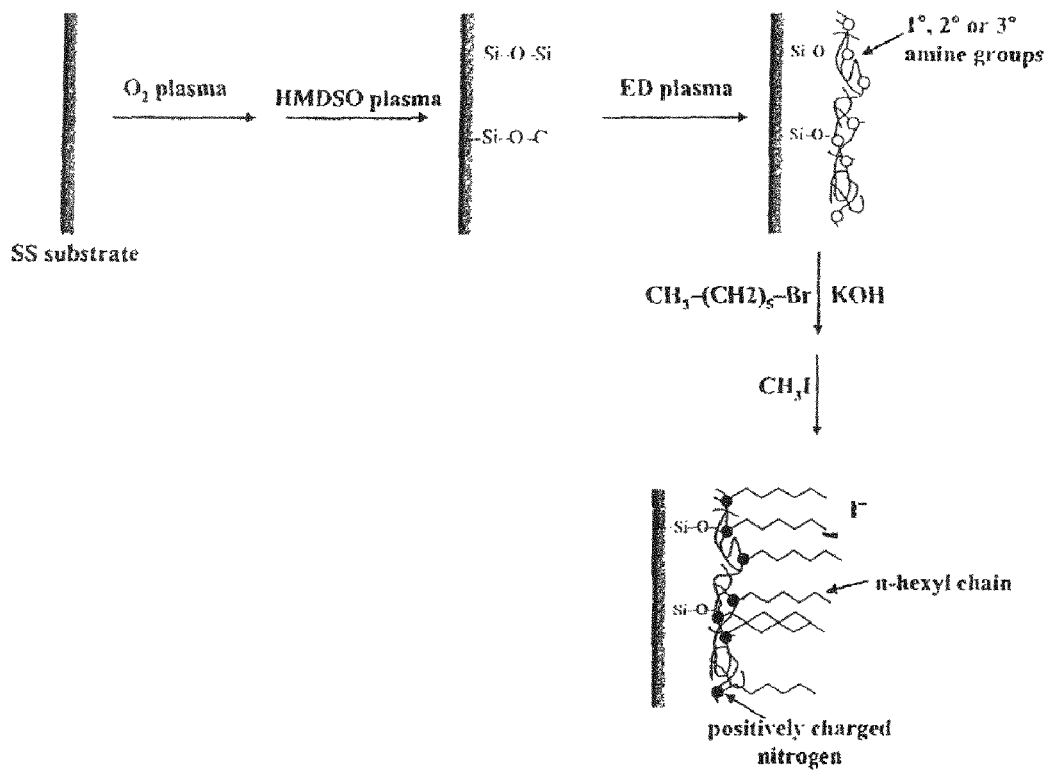
FIG. 3 shows a reaction pathway for the functionalization of the surface of a substrate with quaternary ammonium groups.

In a third embodiment of the present invention, the method for functionalizing the surface of a substrate comprises the steps shown in FIG. 3. This method is particularly well suited for use with stainless steel, cellulose and paper substrates. First, the substrate surface is exposed to an inert plasma under conditions that promote the formation of active sites, such as free-radicals and/or ions, on the surface of the substrate. Suitable inert plasmas include plasmas formed from $O_2$.

The activated substrate surface may then be exposed to a plasma of linker precursor molecules which react with the active sites on the surface to provide linker molecules covalently bound to the surface. However, depending upon the surface, this step may be omitted. For example, cellulose and paper surfaces do not require this step. When this step is included, suitable linker precursor molecules include organosiloxanes, such as hexamethyldisiloxanes (HMDSO), which provide —Si—O—Si and —Si—O—C groups (i.e., linker molecules) bound to the surface of the substrate.

In a subsequent step, the substrate surface active sites, or the surface-bound linker molecules, are reacted with polymer precursor molecules by exposing the substrate surface to a plasma of polymer precursor molecules under conditions which promote the covalent attachment of a polymer layer comprising primary, secondary and/or tertiary amine groups to the surface of the substrate. The polymer precursor molecules are capable both of forming covalent bonds to the plasma-treated substrate or the surface-bound linker molecules and of polymerizing to create a polymer layer comprising amine groups. In some embodiments, the polymer precursor molecules comprise polyamines, such as diamines. An example of a suitable diamine is ethylene diamine.

In a following step of the method, the polymer amine groups are converted to quaternary ammonium groups via alkylation. This step may take place ex situ, that is, by venting the reactor chamber to bring it up to atmospheric pressure and exposing the amine groups to alkyl halide molecules under conditions which promote alkylation of the amine groups. Suitable methods for functionalizing the polymer with quaternary ammoniums groups are describe in Example 4, below. In some embodiments, the quaternary ammonium groups have the formula $-NR_1R_2R_3$, wherein $R_1$, $R_2$ and $R_3$ are independently selected from the group consisting of linear or branched alkyl groups, aryl groups, aralkyl groups, and alkyl, aryl or aralkyl groups substituted with a hydroxyl group or an alkoxy group.

The present invention also provides bactericidal substrates functionalized with quaternary ammonium group-containing polymers. In one embodiment, the bactericidal substrate comprises a quaternary ammonium functionalized polymer layer covalently bound to the surface of the substrate, wherein the quaternary ammonium functionalized polymer may be covalently bound to the substrate surface via —Si—O— groups, as in the case of a stainless steel substrate, or directly to the substrate surface, as in the case of a cellulose substrate In the former case, the quaternary ammonium functionalized polymer does not include —Si—O— in its backbone, these groups are present only as linker molecules which anchor the polymer to the substrate surface.

In general, suitable substrates for the methods and compositions of the present invention include various metals, polymers, and glasses. Examples of suitable metal substrates include stainless steel. Polymer substrates include polyethylene, polypropylene, polyacetal, polyester terephathalate, and polytetrafluoroethylene. Other possible polymers include polycarbonate, polystyrene, polymethylmethacrylate, silicone rubber and cellulose. Cellulose and paper substrates may also be used.

The use of non-equilibrium RF plasmas to covalently attach quaternary ammonium and quaternary phosphonium groups to a wide variety of substrates is further illustrated by the following non-limiting examples.

EXAMPLES

Materials and Methods: Unless otherwise specified, the following materials, equipment, and methods were used in the examples below.

Fluorescamine was purchased from Molecular Probes Inc. (Eugene, Oreg.). Argon and oxygen, used as the gas media for plasma-enhanced reactor-cleaning operations, were obtained from Liquid Carbonic (Brookfield, Wis.). Medical and food grade silicone rubber were obtained from McMaster-Carr Supply Company (Chicago, Ill.). Ethylene diamine, triphenylamine, epichlorohydrin, stainless steel, triphenylphosphine, benzene and cyclohexane were purchased from Aldich Co.

All silicone rubber substrates were cut into 1×1×0.2 cm samples. The silicone rubber chips were washed in a hot alkaline detergent (Micro; International Products, Trenton, N.J.) for 30 minutes, rinsed five times in distilled water, and air dried before use. Polypropylene substrate films were cut into 1 inch diameter disks and used without further cleaning.

Unmodified and plasma-modified surfaces were analyzed by survey and high resolution electron spectroscopy for chemical analysis (HR ESCA) to determine the relative surface atomic concentrations and the relative ratios of carbon, oxygen, silicon, and nitrogen atoms present in non-equivalent atomic environments. ESCA was performed using a Perkin-Elmer Physical Electronics 5400 Small Area Spectrometer under the following conditions: Mg source; 15 kV; 300 W; pass energy=89.45 eV; angle=45° (Perkin-Elmer, Palo Alto, Calif.). Carbon ($C_{1s}$), oxygen ($O_{1s}$), silicon ($Si_{2p}$), and nitrogen ($N_{1s}$) atomic compositions were evaluated and the peaks corresponding to atoms located in non-equivalent positions were analyzed. To correct for surface-charge-origin binding energy shifts, calibrations were performed based on the well-known C—O—C ($C_{1s}$) and Si—C ($Si_{2p}$) peaks.

In some cases, functionalized surfaces were also evaluated using a fluorescamine test. In the test, primary aliphatic amine functionalities were labeled with fluorescamine, which reacts with primary amine groups to generate a complex which absorbs at 381 nm and fluoresces at 470 nm. Substrates to be analyzed were sprayed 3 times consecutively with a fluorescamine solution (25 mg fluorescamine in 100 ml acetone) using a Gelman Chromist aerosol propellant attached to polypropylene bottle. The fluorescamine-coated substrates were exposed to a Black-Ray UV-lamp, model UBL 21 (UVP Inc. San Gabriel, Calif.) and the fluorescence was detected using a FCR-10 photo camera (Fotodyne Inc., Hartland, Wis.). Photographic imaging may be used to qualitatively evaluate the surfaces or fluorescence intensity can be measured quantitatively using a calibrated fluorescence spectrometer.

Example 1

Attachment of Quaternary Ammonium Groups to a Polymeric Substrate

Substrate surfaces were decorated with covalently-bound quaternary ammonium functionalities by generation of oxirane groups using epichlorhydrin on argon-plasma activated polymer surfaces, followed by in situ gas-phase reaction of the epoxy functionalities with triethylamine in the absence of plasma. Typically, polypropylene samples were exposed to an argon plasma (200 mTorr, 200 W) for one minute followed by in situ reaction with epichlorihydrin at 1 Torr for 30 minutes. Samples were then immersed in a mixture of equal parts triethylamine and sodium hydroxide and one tenth part methanol for 8 hours at 15° C.

Comparison of deconvoluted HR ESCA spectra from untreated polypropylene surfaces with spectra obtained from epoxy functionalized polypropylene surfaces and quaternary ammonium functionalized polypropylene surfaces demonstrate the presence of oxirane and C—N groups on the functionalized surfaces. Assignment of C—N binding energy peaks and the $N_{1s}$ binding energy of quaternary ammonium functionalities was based on the survey and HR ESCA spectra of model compounds such as poly(ethyleneimine) ($C_{1s}$ C—N: 285.5 eV; $N_{1s}$ N=399 eV), poly(allylamine hydrochloride) ($C_{1s}$ C—N=286.2 eV and $N_{1s}$ N=401.5 eV), and poly(vinylbenzylethylammonium chloride) ($C_{1s}$ C—N=286 eV and $N_{1s}$ N=402.1 eV) according to ESCA database data. The binding energy peaks of the quaternary ammonium functionalized surfaces ($C_{1s}$ (C—N=286.7 eV) and $N_{1s}$ (N=402 eV)) were significantly higher than those of poly(ethyleneimine) and similar to those of poly(allylamine hydrochloride) and poly(vinylbenzylethylammonium chloride) suggesting that polypropylene surfaces have been successfully functionalized with quaternary ammonium groups.

The epoxy functionalized polypropylene surfaces were also evaluated using the fluorescamine test. Surface-bound oxirane groups were reacted in situ with ethylenediamine and then exposed to a fluorescamine solution. Untreated polypropylene and epoxy functionalized polypropylene surfaces were also exposed to a fluorescamine solution and the fluorescence of the three surfaces compared. Photographic images of the surfaces showed negligible fluorescence from the untreated and epoxy functionalized polypropylene surfaces. The epoxy functionalized surface that had been further reacted with ethylenediamine showed significant fluorescence, indicating the presence of primary amine groups and confirming that epoxy functionalities had been successfully covalently attached to the polypropylene surfaces.

Example 2

Plasma Deposition of Allyl Chloride onto Substrate Surfaces

A polymer was formed on the activated substrate surfaces by plasma deposition of allyl chloride. Substrates included 50 Whatman filter paper, cellophane, stainless steel, and glass. The plasma parameters were as follows: Base pressure=32 mTorr; Pressure of allyl chloride=200 mTorr; RF frequency=13.56 MHz; RF power=60 W; treatment time=3 minutes; period=55 ms and 100 ms; plasma-on-time=5 ms; plasma-off-time=95 ms. After plasma deposition, the plasma reactor was evacuated to base pressure and post plasma quenching of free radicals was performed by reacting allyl chloride in situ at 10 Torr for 30 minutes. The samples were then removed, washed repeatedly with benzene and cyclohexane, and stored for further analysis and/or functionalization reactions.

The influence of certain plasma parameters on the chemical composition of the allyl chloride polymer layer deposited on substrate surfaces was investigated. The impact of RF power and duty cycle (plasma-on-time and plasma-off-time) on the chemical composition of the deposited allyl chloride layer is shown in Table 1. Although the RF power dissipated to the electrodes does not have a significant influence on the relative chlorine surface concentration, the longer the plasma-off-time, the higher the chlorine concentration. Table 2 shows the effect of the total treatment time on the chemical composition of the thin polymer layer. Varying the total treatment time did not generate a significant change in the relative surface atomic concentrations, suggesting that a stable plasma-induced reaction mechanism controls the deposition process.

TABLE 1

Impact of plasma parameters on the chemical composition of deposited allyl chloride layers.

| Experiment number | Power (watts) | Duty Cycle ms ON/ms OFF | Carbon (%) | Oxygen (%) | Chloride (%) |
| --- | --- | --- | --- | --- | --- |
| 1 | 90 | 5/140 | 82.8 | 3.5 | 13.7 |
| 2 | 30 | 5/140 | 83.5 | 2.1 | 14.4 |

TABLE 1-continued

Impact of plasma parameters on the chemical composition of deposited allyl chloride layers.

| Experiment number | Power (watts) | Duty Cycle ms ON/ms OFF | Carbon (%) | Oxygen (%) | Chloride (%) |
|---|---|---|---|---|---|
| 3 | 90 | 5/50 | 84.4 | 2.4 | 13.3 |
| 4 | 30 | 5/50 | 85.1 | 2.1 | 12.8 |
| 5 | 102 | 5/95 | 84.8 | 2.4 | 12.8 |
| 6 | 18 | 5/95 | 81.3 | 7.3 | 11.4 |
| 7 | 60 | 5/159 | 83.6 | 3.1 | 13.3 |
| 8 | 60 | 5/31 | 85.9 | 3.6 | 10.5 |
| 9 | 60 | 5/95 | 84.1 | 2.8 | 13.1 |
| 10 | 60 | 5/95 | 82.1 | 7.2 | 10.7 |
| 11 | 60 | 5/95 | 80.7 | 9.5 | 9.8 |
| 12 | 60 | 5/95 | 84.2 | 43 | 11.1 |
| 13 | 60 | 5/95 | 84.7 | 3.5 | 11.9 |

TABLE 2

Impact of total treatment time on the chemical composition of deposited allyl chloride layers.

| Experiment number | Time (min) | Carbon (%) | Oxygen (%) | Chloride (%) |
|---|---|---|---|---|
| 1 | 0.5 | 83.2 | 4.1 | 12.7 |
| 2 | 1 | 86.3 | 3.7 | 10.0 |
| 3 | 2 | 86.9 | 3.9 | 10.2 |
| 4 | 3 | 83.2 | 4.1 | 12.0 |
| 5 | 4 | 83.2 | 3.7 | 13.1 |
| 6 | 1 | 86.3 | 3.8 | 9.8 |
| 7 | 4 | 84.0 | 3.3 | 12.8 |

Experimental data suggest that an allyl chloride polymer layer has been successfully covalently attached to substrate surfaces. HR ESCA spectra show multimodal peaks dominated by C—C bonds (285 eV) with smaller, but obvious, C—O (286.5 eV) and C—Cl (287.3 eV) binding energy peaks.

A significant increase in concentration of Cl and a substantial decreases in concentration of C in plasma-deposited polymer layers relative to theoretical values was also observed. This suggests that plasma-induced dechlorination and/or dehydrochlorination reactions have resulted in the generation of stable C—Cl bonds (non-allylic) in addition to Cl- and H-loss processes, through molecular rearrangement and recombination mechanisms.

The presence of oxygen atoms in the structure of plasma-deposited allyl chloride layers may be explained by post-plasma oxidation reactions in open laboratory environments initiated by the plasma-generated free radicals. Because ESCA can probe to about 100 Å, however, depending upon the thickness of the plasma-deposited allyl chloride polymer, the ESCA data may reflect some of the characteristics of the underlying substrate material.

Example 3

Attachment of Quaternary Phosphonium Groups to Substrate Surfaces

Substrate surfaces that had been treated with plasma-deposited allyl chloride were further decorated with covalently-bound quaternary phosphonium functionalities by ex situ reaction of the allylic chlorine functionalities with triphenylphosphine. The allyl chloride polymer-coated substrates were immersed in a triphenylphosphine/benzene solution and the reaction mixture was stirred for 24 hours at 80° C. Samples were moved, washed with benzene and cyclohexane, and dried.

ESCA data is shown in Tables 3-4. Table 3 provides the chemical composition of substrates that had not been washed with benzene and cyclohexane prior to plasma deposition of allyl chloride. Table 4 shows similar data for substrates that had been washed prior to plasma deposition. Finally, Table 5 shows the chemical composition of substrates that were washed, treated with plasma-deposited allyl chloride, and further treated with triphenylphosphine.

TABLE 3

Chemical composition of substrates that had not been washed prior to plasma-deposition of allyl chloride

| | Atomic concentration | | | |
|---|---|---|---|---|
| Sample | C (%) | O (%) | Cl (%) | P (%) |
| PR[ACL] | 86.6 | 2.5 | 13.5 | — |
| CE[ACL] | 84.0 | 1.5 | 14.5 | — |
| SS[ACL] | 79.0 | 5.6 | 14.1 | — |
| GL[ACL] | 80.1 | 5.2 | 14.3 | — |

[ACL] = plasma-deposited allyl chloride;
PR = paper;
CE = cellophane;
SS = stainless steel;
GL = glass

TABLE 4

Chemical composition of substrates that had been washed prior to plasma-deposition of allyl chloride

| | Atomic concentration | | | |
|---|---|---|---|---|
| Sample | C (%) | O (%) | Cl (%) | P (%) |
| WAPR[ACL] | 71.1 | 20.8 | 8.1 | — |
| WACE[ACL] | 82.1 | 4.6 | 13.2 | — |
| WASS[ACL] | 81.3 | 5.6 | 13.1 | — |
| WAGL[ACL] | 81.1 | 5.9 | 14.1 | — |

WA = washed;
[ACL] = plasma-deposited allyl chloride;
PR = paper;
CE = cellophane;
SS = stainless steel;
GL = glass

TABLE 5

Chemical composition of substrates that had been washed prior to plasma-deposition of allyl chloride and then functionalized with triphenylphosphine

| | Atomic concentration | | | |
|---|---|---|---|---|
| Sample | C (%) | O (%) | Cl (%) | P (%) |
| WAPR[ACL] P(Ph)$_3$Cl | 63.1 | 31.3 | 4.2 | 1.1 |
| WACE[ACL]P(Ph)$_3$Cl | 82.1 | 7.7 | 8.4 | 1.0 |
| WASS[ACL] P(Ph)$_3$Cl | 85.7 | 3.6 | 9.5 | 1.1 |
| WAGL[ACL] P(Ph)$_3$Cl | 85.1 | 4.4 | 9.3 | 1.2 |

Ph(Ph)3Cl = quaternary phosphonium group;
WA = washed;
[ACL] = plasma-deposited allyl chloride;
PR = paper;
CE = cellophane;
SS = stainless steel;
GL = glass The ESCA data revealed that substrates that were washed prior to plasma deposition of allyl chloride exhibit a higher relative surface concentration of atomic oxygen. (Tables 3 and 4.) The increased oxygen concentration may be due to the removal of hydrocarbon surface contaminants during the washing procedure, which may facilitate post-plasma oxidation reactions. Both washed and non-washed substrates, however, have comparable relative chlorine concentrations. (Tables 3 and 4.) Finally, ESCA data from substrates coated with an allyl chloride polymer layer and further treated with triphenylphosphine indicate the presence of phosphorous atoms on all substrates, suggesting that substrate surfaces have been successfully functionalized with quaternary phosphonium groups.

Example 4

Attachment of Quaternary Ammonium Groups to Stainless Steel and Cellulose Substrates Stainless steel substrates were pretreated by exposing them to an $O_2$ plasma (300 mTorr, 300 W, 5 min.) followed by exposure to an HMDSO plasma (200 mTorr, 200 W, 1 min.). Cellulose substrates were not pretreated. The stainless steel and cellulose substrates were then exposed to a plasma of ethylene diamine at 200 mTorr, 100 W at 13.56 MHz RF power (continuous wave mode) for 10 minutes to provide a layer of polymer covalently bound to the substrates. The polymer amine groups were alkylated with hexyl bromide in amyl alcohol and KOH for 12 hours. After rising with methanol, the polymer was further reacted with iodomethane in amyl alcohol for another 12 hours. The reaction pathway is illustrated in FIG. 3. The films were covalently attached and did not laminate by washing with acetone or water. ESCA data from the substrates confirmed the presence of quaternary ammonium groups.

What is claimed is:

1. A bactericidal substrate comprising:
    (a) a substrate having a surface; and
    (b) quaternary ammonium functionalized molecules covalently bound to the surface, wherein the quaternary ammonium functionalized molecules have the formula —$(CH_2)_n$—$CH(OH)$—$(CH_2)_m$—$NR_1R_2R_3$,
    wherein n is an integer from 0 to 20,
    m is an integer from 1 to 20, and
    $R_1$, $R_2$ and $R_3$ are independently selected from the group consisting of linear or branched alkyl groups, aryl groups, aralkyl groups, and alkyl, aryl or aralkyl groups substituted with a hydroxyl group or an alkoxy group,
    and further wherein the quaternary ammonium functionalized molecules are each directly covalently bonded to the surface at one end and terminated by a quaternary ammonium mgroup at the opposite end.

2. The substrate of claim 1, wherein the surface comprises a metal.

3. The substrate of claim 2, wherein the metal comprises stainless steel.

4. The substrate of claim 1, wherein the surface comprises a polymer.

5. The substrate of claim 4, wherein the polymer is selected from the group consisting of polyethylene, polypropylene, polyacetal, polyethylene terephthalate, and polytetrafluoroethylene.

6. The substrate of claim 4, wherein the polymer is selected from the group consisting of polycarbonate, polystyrene, polymethylmethacrylate, silicone rubber and cellulose.

7. The substrate of claim 1, wherein the surface comprises glass.

8. A method for forming a bactericidal substrate, the method comprising:
    forming active sites on a substrate having a surface by exposing the substrate surface to a plasma;
    reacting a gas comprising linker molecules with the active sites in situ in the absence of plasma to provide surface-bound linker molecules; and
    reacting the surface-bound linker molecules with quaternary ammonium precursor molecules to provide quaternary ammonium functionalized molecules covalently bound to the surface, wherein the quaternary ammonium functionalized molecules have the formula —$(CH_2)_n$—$CH(OH)$—$(CH_2)_m$—$NR_1R_2R_3$,
    wherein n is an integer from 0 to 20,
    m is an integer from 1 to 20, and
    $R_1$, $R_2$ and $R_3$ are independently selected from the group consisting of linear or branched alkyl groups, aryl groups, aralkyl groups, and alkyl, aryl or aralkyl groups substituted with a hydroxyl group or an alkoxy group,
    and further wherein the quaternary ammonium functionalized molecules are each directly covalently bonded to the surface at one end and terminated by a quaternary ammonium group at the opposite end.

9. The method of claim 8, wherein the linker molecules are epoxy-functional molecules.

10. The method of claim 9, wherein the epoxy-functional molecules are epihalohydrin molecules.

11. The method of claim 8, wherein the quaternary ammonium precursor molecules have the formula $NR_1R_2R_3$, wherein $R_1$, $R_2$ and $R_3$ are independently selected from the group consisting of linear or branched alkyl groups, aryl groups, aralkyl groups, and alkyl, aryl or aralkyl groups substituted with a hydroxyl group or an alkoxy group.

* * * * *

UNITED STATES PATENT AND TRADEMARK OFFICE
CERTIFICATE OF CORRECTION

| | | |
|---|---|---|
| PATENT NO. | : 8,029,902 B2 | Page 1 of 1 |
| APPLICATION NO. | : 11/609045 | |
| DATED | : October 4, 2011 | |
| INVENTOR(S) | : Ferencz S. Denes et al. | |

It is certified that error appears in the above-identified patent and that said Letters Patent is hereby corrected as shown below:

IN THE SPECIFICATION:

Col. 3; line 52

Delete the phrase "The plasma-chemist approach" and replace with -- The plasma-chemistry approach --

Col. 11; line 40

Delete the phrase "decreases in concentration" and replace with -- decrease in concentration --

Col. 11; line 66

Delete the phrase "Samples were moved" and replace with -- Samples were removed --

IN THE CLAIMS:

Col. 13; line 50 (Claim 1)

Delete the phrase "mgroup at the opposite end" and replace with -- group at the opposite end --

Signed and Sealed this
Seventeenth Day of January, 2012

David J. Kappos
*Director of the United States Patent and Trademark Office*